US010653864B2

(12) United States Patent
Piyatilake et al.

(10) Patent No.: US 10,653,864 B2
(45) Date of Patent: May 19, 2020

(54) CATCH AND RELEASE DEVICE

(71) Applicants: Mahinda Dwayne Piyatilake, Skokie, IL (US); Kishani Chamila Piyatilake, Skokie, IL (US)

(72) Inventors: Mahinda Dwayne Piyatilake, Skokie, IL (US); Kishani Chamila Piyatilake, Skokie, IL (US)

( * ) Notice: Subject to any disclaimer, the term of this patent is extended or adjusted under 35 U.S.C. 154(b) by 0 days.

(21) Appl. No.: 15/858,258

(22) Filed: Dec. 29, 2017

(65) Prior Publication Data
US 2018/0193602 A1 Jul. 12, 2018

Related U.S. Application Data

(60) Provisional application No. 62/498,893, filed on Jan. 11, 2017.

(51) Int. Cl.
*F16L 3/22* (2006.01)
*A61M 25/02* (2006.01)
*H01R 13/58* (2006.01)
*A61M 5/14* (2006.01)
*A61M 5/158* (2006.01)

(52) U.S. Cl.
CPC ......... *A61M 25/02* (2013.01); *H01R 13/5812* (2013.01); *H01R 13/5833* (2013.01); *A61M 2005/1416* (2013.01); *A61M 2005/1586* (2013.01); *A61M 2025/024* (2013.01); *A61M 2025/026* (2013.01); *A61M 2025/0206* (2013.01)

(58) Field of Classification Search
CPC .............. F16L 3/221; F16L 3/22; F16L 3/222
See application file for complete search history.

(56) References Cited

U.S. PATENT DOCUMENTS

| 6,290,676 | B1 | 9/2001 | Bierman | |
|---|---|---|---|---|
| 8,505,170 | B1 | 8/2013 | Gray et al. | |
| 8,900,196 | B2 * | 12/2014 | Andino | A61M 5/1418 604/174 |
| 9,248,260 | B2 | 2/2016 | Khalaj | |
| 9,534,708 | B2 * | 1/2017 | Cripps, II | F16L 3/222 |
| 2007/0120023 | A1 * | 5/2007 | Martinez | E02F 9/2275 248/75 |

* cited by examiner

*Primary Examiner* — Amy J. Sterling
(74) *Attorney, Agent, or Firm* — Dunlap Bennett & Ludwig PLLC

(57) ABSTRACT

A retaining device is disclosed. The retaining device is made of suitable material formed in a frame having a central portion and two opposing arms spaced apart from the frame and in the plane thereof. The central portion being arranged so as to cause a conduit inserted through the cord slots between the central portion and the opposing arms to be urged substantially equally against the opposing arms. Each opposing arm provides a tapered gripping edge directed toward the central portion, wherein each gripping edges provides a plurality of serrations for further engaging the urged conduit.

8 Claims, 4 Drawing Sheets

CATCH AND RELEASE DEVICE

CROSS-REFERENCE TO RELATED APPLICATION

This application claims the benefit of priority of U.S. provisional application No. 62/498,893, filed 11 Jan. 2017, the contents of which are herein incorporated by reference.

BACKGROUND OF THE INVENTION

The present invention relates to clips and, more particularly, to a catch and release device, apparatus and methods of holding and supporting different diameter conduits, such as medical air lines, earphone or headset lines, wires, and power cords in a clip that can attach to any suitable movable or immovable object.

Since conduits are ubiquitous because they play a vital role in many industries, including the medical field, manufacturing, defense, electronics and the like, their accidental disconnection and/or loss of signal can cause critical disruptions.

For example, in medical devices, intravenous (IV) and monitoring lines may be accidentally removed through spasms and/or seizures in the patient or through other abrupt linear motion, where such unintentionally disruptions could be fatal or cause a tear in the tissue at the point of entry into the body. In electronics, accidental removal of inputs and output leads can result in loss of power, feed, signal, short circuiting, and the like.

As can be seen, there is a need for a quick catch and release device/hook that could prevent an accidental disruption of a conduit in the electrical, medical, and other arts, thereby preserving the wellbeing of the patient/machine/process. This device/hook/hoop can be used in all situations when such a need is required to catch and release a conduit in a quick and timely manner, in such fields listed below and more.

For medical devices, the present invention may attach to patients in such a way as to prevent the intravenous needle from accidentally coming out of the point of entry and/or causing a tear in the tissue. In the electronic arts, the present invention could be used individually or in series to harness and thus prevent accidental removal of inputs and output leads, wiring and cables. In the music field, the present invention can be used to prevent the loss of signal (electrical) and damage (torque) to the instrument/device. In manufacturing, the present invention can be used to secure cables and wire from vibrating, loosing feed and coming loose. In sports, the present invention may be used where a speedy catch and release is a required, i.e., mountain climbing, rock climbing, cycling, kayaking, skiing, etc. In personal audio, the present invention may be used where a catch and release device is required for, say, preventing earbuds and head phones cables/leads from being yanked out from the ear or being subject to sudden linear motion thereby breaking the signal of the electronic devices. In aviation/avionics/maritime/transport, the present invention may be used to harness electrical cables and wires from chafing and short circuiting, securing cargo straps/restraints from coming loose, and the like. In photography, defense industry and law enforcement the present invention can be used in all situations where speedy catch and release is a required, straps, etc.

SUMMARY OF THE INVENTION

In one aspect of the present invention, a retaining device includes a flexible material formed in a frame having a central portion and two opposing arms spaced apart from the frame and in the plane thereof so as to form two opposing cord slots; and the central portion being arranged so as to cause a conduit inserted through both cord slots to be urged substantially equally against the opposing arms.

In another aspect of the present invention, the retaining device further includes a hook portion extending from each of both opposing ends of the frame; both hook portions turning back toward each other so as to be planar with the frame, defining a cavity therebetween, wherein the cavity has a generally symmetrical shape.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a catch and release device of suitable material formed in a frame having a central portion and two opposing arms spaced apart from the frame and in the plane thereof. The central portion being arranged so as to cause a conduit inserted through the cord slots between the central portion and the opposing arms to be urged substantially equally against the opposing arms. Each opposing arm provides a tapered gripping edge directed toward the central portion, wherein each gripping edges provides a plurality of serrations for further engaging the urged conduit.

Referring to FIGS. 1 through 12, the present invention may include a catch and release device 100 made of material that can be repeatedly bent without fracturing, such as polyethylene, polypropylene, vinyl, nylon, rubber, leather, various impregnated or laminated fibrous materials, various plasticized materials or other suitable materials that can be cut using a laser cut, punched press, guillotined, 3D printed, additively manufactured, or any other suitable process. The material may be coated, sterilized, packed and provided in numerous materials sizes and colors.

Figure 1:
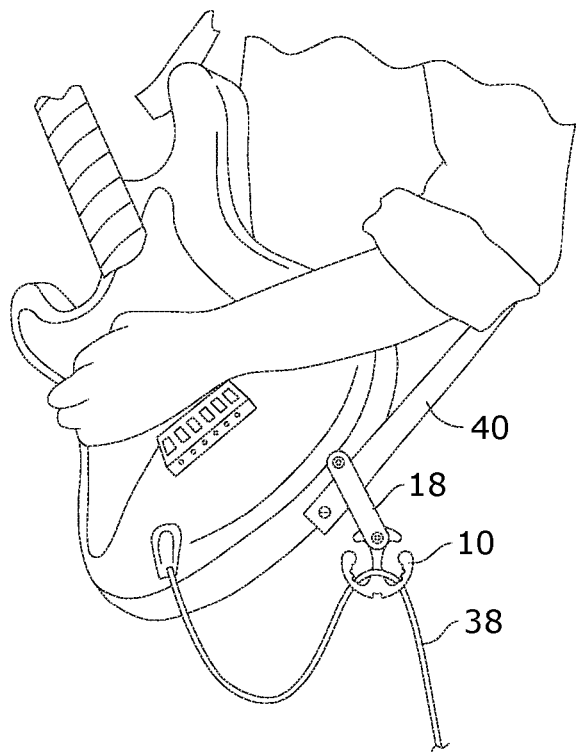
FIG. 1 is a perspective view of an exemplary embodiment of the present invention shown in use.
Figure 2:
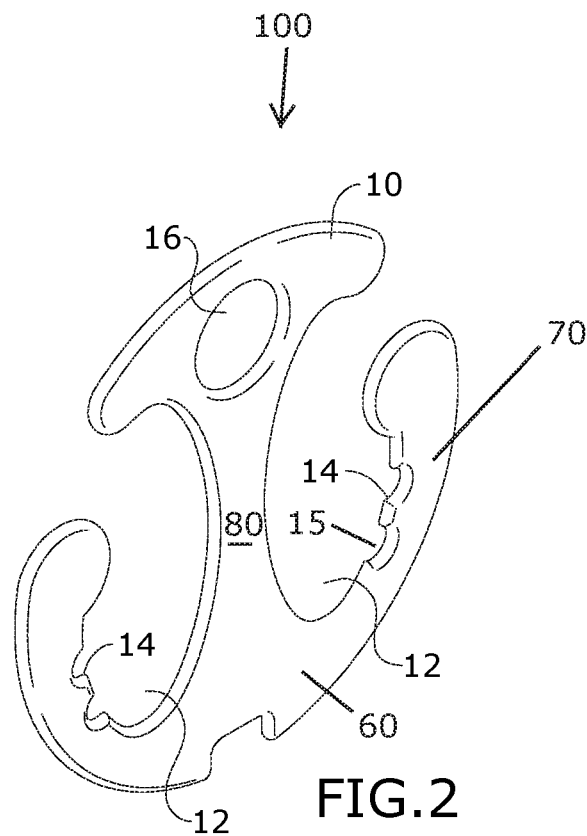
FIG. 2 is a perspective view of an exemplary embodiment of the present invention.
Figure 3:
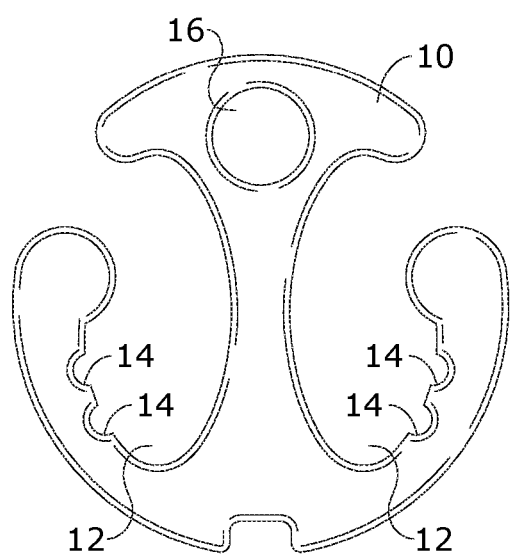
FIG. 3 is a front elevation view of an exemplary embodiment of the present invention.
Figure 4:
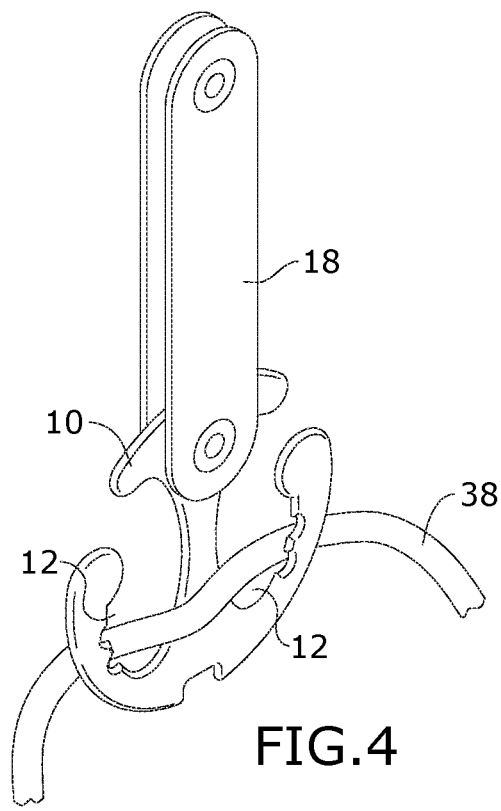
FIG. 4 is a perspective view of an exemplary embodiment of the present invention, shown in use.

Referring to FIGS. 1 and 4, the suitable material may be formed in a frame 60 having a central portion 80 and two opposing arms 70 spaced apart from the frame 60 and in the plane thereof, said central portion 80 being arranged so as to cause a conduit 38 or 42 inserted between said central portion 80 and said opposing arms 70 to be urged substantially equally against the opposing arms 70. Cord slots 12, 22, 32, or 46 may be defined by the space between each opposing arm 70 and the central portion 80, each cord slot 12, 22, 32, or 46 adapted to receive the conduit 38 or 42.

Each arm 70 may provide tapered gripping edges 14, 24, 34, 48 facing inward toward each other. Each gripping edges 14, 24, 34, 48 may provide at least one semi-circular serration 15 adapted to engage and thus prevent conduits 38 or 42 from accidentally releasing through linear motion or the like. The central portion 80 may have an attachment hole 16 or 26 for engaging, directly or indirectly, an attachment object 18 or 40, as illustrated in FIG. 4.

Figure 5:
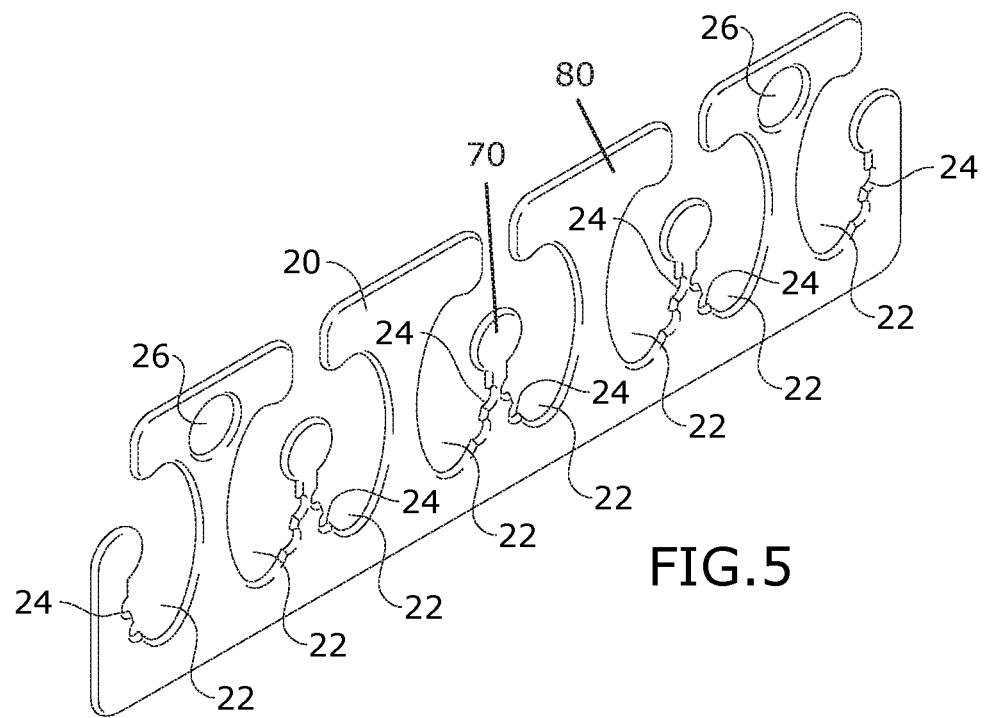
FIG. 5 is a perspective view of an exemplary embodiment of the present invention.
Figure 6:
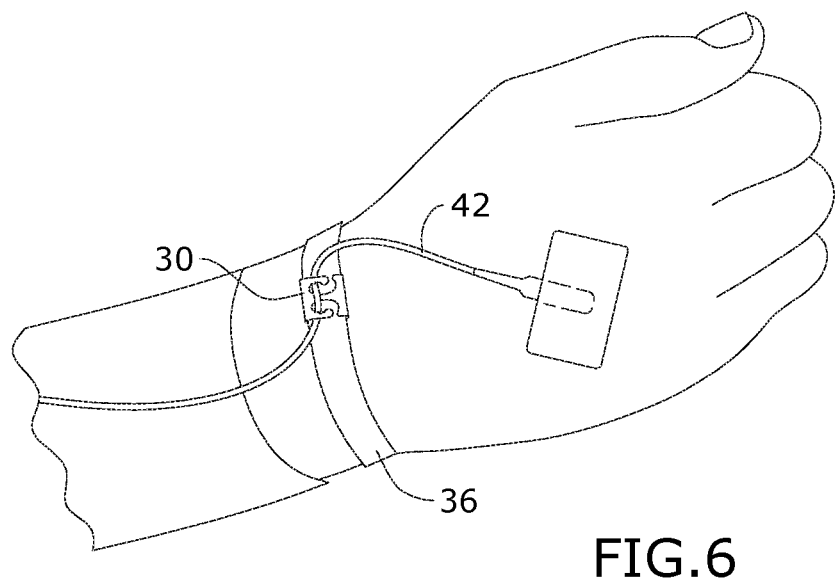
FIG. 6 is a perspective view of an exemplary embodiment of the present invention, shown in use.
Figure 7:
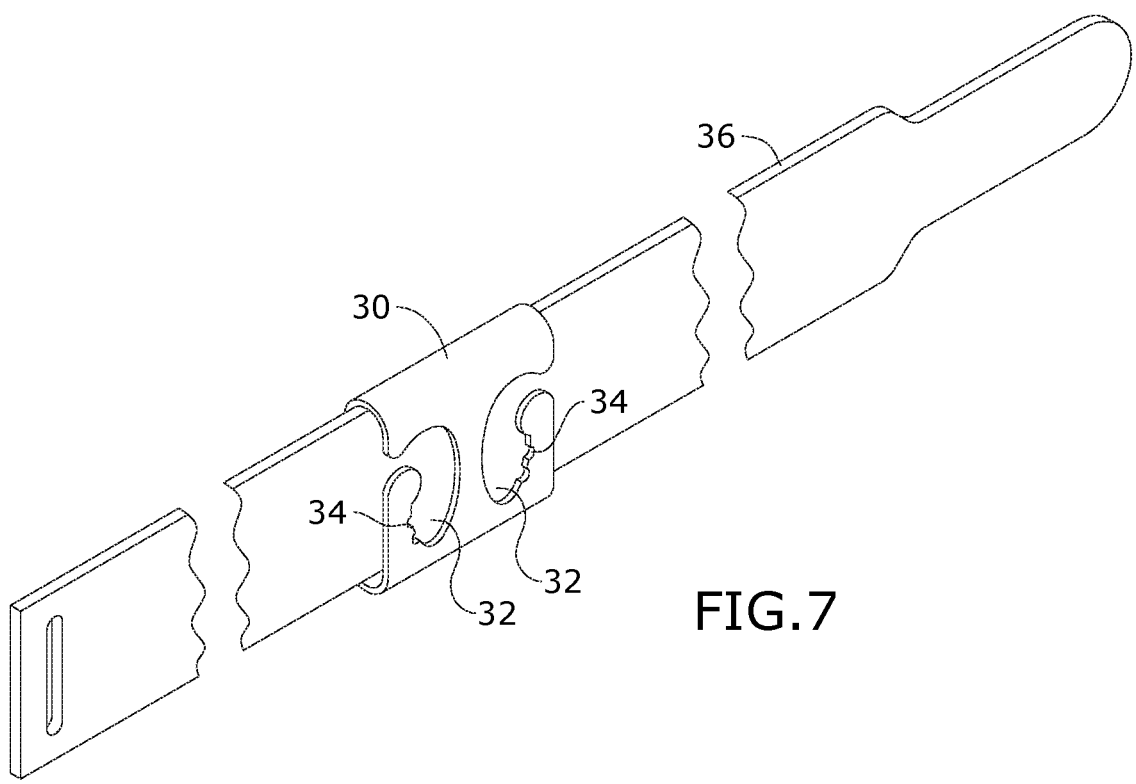
FIG. 7 is a perspective view of an exemplary embodiment of the present invention.
Figure 8:
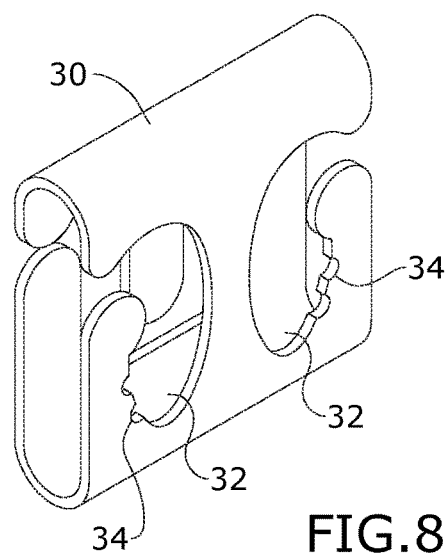
FIG. 8 is a front perspective view of hook portion of an exemplary embodiment of the present invention.
Figure 9:
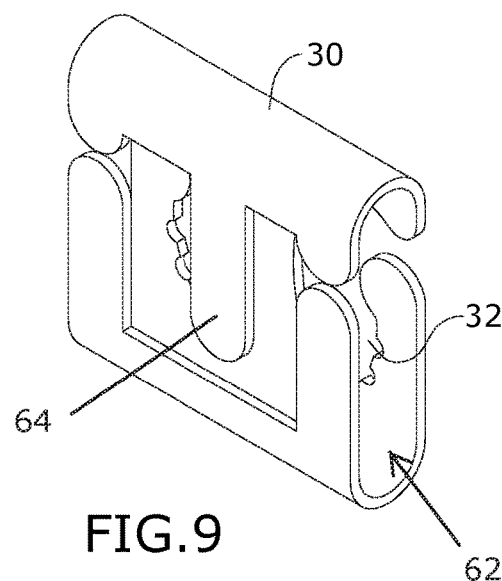
FIG. 9 is a rear perspective view of hook portion of an exemplary embodiment of the present invention.

Referring to FIG. 5, in certain multi-cord harness 20 embodiments a plurality of frames 60 may be sequentially joined along adjacent arm portions, wherein one arm 70 may act as an opposing arm 70 for two adjacent central portions. The multi-cord harness 20 being adapted to removably secure a plurality of conduits 38 and/or 42 simultaneously. The multi-cord harness 20 that can be anchored to a surface either moveable/immovable, through which the conduits may be passed, or alternatively the multi-cord harness 20 engages. An example of such an application would be house wiring.

Referring to FIGS. 6-9, in certain hooked embodiments, the frame 60 provides a hooked portion 30. The hooked portion 30 may extend from two opposing ends of the frame 60, each extended end turning back toward each other so as to be generally parallel with the original frame 60, whereby a cavity 62 is provided between the frame 60 and the hooked portion 30. The cavity 62 being dimensioned and adapted to slidably receive a bracelet 36 or 52 or other attachment object, such as a strap. The hook portion 30 may define a tongue and opening 64 arrangement for further engaging the bracelet 36 or 52 or other attachment object received through the cavity 62.

Figure 10:
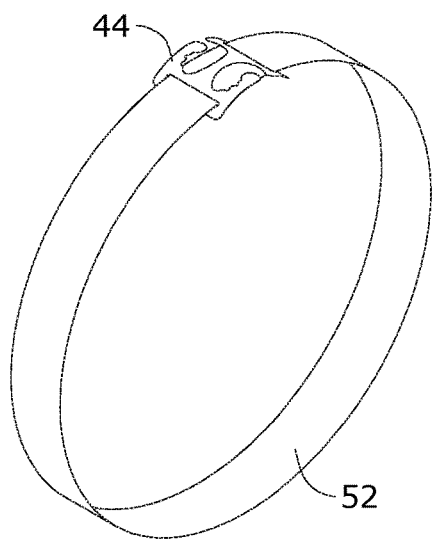
FIG. 10 is a perspective view of an exemplary embodiment of the present invention.
Figure 11:
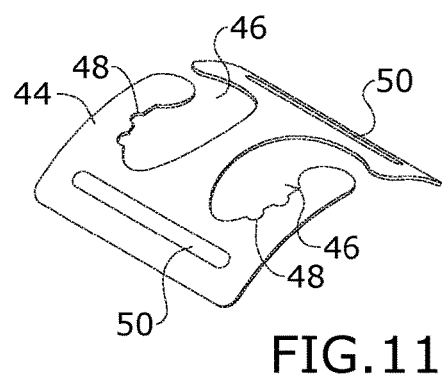
FIG. 11 is a front perspective view of a bent slotted exemplary embodiment of the present invention.
Figure 12:
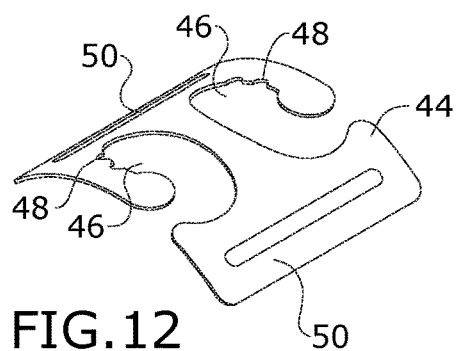
FIG. 12 is a rear perspective view of the bent slotted exemplary embodiment of the present invention.

Referring to FIGS. 10-12, in certain bent slotted 44 embodiments, the frame 60 may have a curvature. The opposing ends of the bent slotted 44 may provide slots 50 for slidably receiving a bracelet 36 or 52 or other attachment object, such as a strap.

A method of using the present invention may include the following. The catch and release device 10 disclosed above may be provided. A user may, in context of the medical field, place the catch and release device 10 around the patient's wrist and/or arm and locked in to place using an adhesive strip or by way of engaging bracelet 36 or 52 or other attachment object, such as a strap, as described above. The catch and release device 10 may be best kept separated or isolated from the point where it is required. The conduit 38 or 40 may be slid through the cord slots and hooked around the central portion 80 and opposing arm 70 so as to cause the conduit 38 or 42 inserted therebetween to be urged substantially equally against the opposing arms 70. At least one semi-circular serration 15 of each gripping edge 14, 24, 34, 48 may engage aid urged conduit 38 or 42, thereby preventing critical feeds from accidentally releasing. This present invention can be used in all situations when such a need is required to catch and release various tubular material/conduits in a quick and timely manner.

It should be understood, of course, that the foregoing relates to exemplary embodiments of the invention and that modifications may be made without departing from the spirit and scope of the invention as set forth in the following claims.

What is claimed is:

1. A device comprising:
   flexible material formed in a frame, the frame comprising:
   a central portion;
   two arms spaced apart from the central portion and in the plane thereof so as to form two opposing cord slots;
   each cord slot defined by a semioval outer periphery of the central portion and a serrated inner periphery of one of the two arms;
   each arm having a bulbous distal end having a width greater than any other portion of said arm, wherein the bulbous distal end protrudes into the cord slot; and
   the central portion being arranged so as to cause a conduit simultaneously disposed through the two opposing cord slots are urged substantially equally against the two arms, and wherein said conduit is engaged by a portion of said serrated inner periphery of each of the two arms.

2. The device of claim 1, wherein the two arms are symmetrically curved relative to the central portion.

3. The device of claim 1, further comprising at least one semicircular serration provides along each serrated inner periphery.

4. The device of claim 1, wherein opposing ends of the frame define a curvature across the frame, a slot provided inward of each opposing end.

5. The device of claim 1, further comprising an attachment hole provided by the central portion.

6. The device of claim 1, further comprising a hook portion extending from each of both opposing ends of the frame; both hook portions turning back toward each other so as to be planar with the frame, defining a cavity therebetween.

7. The device of claim 6, wherein the cavity has a generally symmetrical shape.

8. The device of claim 6, further comprising a tongue and opening arrangement provided by both hook portions.

* * * * *